United States Patent [19]

Pisanchyn et al.

[11] 3,931,343

[45] Jan. 6, 1976

[54] NITROSOCHLORINATION OF CYCLO-OLEFINS

[75] Inventors: John Pisanchyn, Morristown; Stylianos Sifniades, Madison; Robert Fuhrmann, Morris Plains; Fred W. Koff, Clifton, all of N.J.

[73] Assignee: Allied Chemical Corporation, New York, N.Y.

[22] Filed: Feb. 11, 1974

[21] Appl. No.: 441,610

[52] U.S. Cl. ............................................... 260/647
[51] Int. Cl.² ................................................ C07C 81/00
[58] Field of Search ..................................... 260/647

[56] References Cited
UNITED STATES PATENTS 2,485,180  10/1949  Allison ............................... 260/647
3,714,255  1/1973  Olechowski ........................ 260/647

Primary Examiner—Leland A. Sebastian
Attorney, Agent, or Firm—Arthur J. Plantamura

[57] ABSTRACT

Cyclo-olefins are converted in high yield to the corresponding chloro-nitroso dimers by dissolving the cyclo-olefin in liquid $SO_2$ and contacting with NOCl while maintaining a substantially oxygen-free environment. Even higher yields are attained by controlling the gradual addition of the NOCl and by using a molar ratio of NOCl to cyclo-olefin of less than about 0.92:1.

6 Claims, No Drawings

NITROSOCHLORINATION OF CYCLO-OLEFINS

BACKGROUND OF THE INVENTION

I. Field of the Invention

This invention relates to an improvement in a method for converting cyclo-olefins to nitrosochlorides, particularly for converting cyclo-olefins to the corresponding chloronitrosodimers using sulfur dioxide as solvent. These dimers are useful as monomer precursors for polyamides or in a variety of other applications. In particular, the 2-chloro-1-nitrosocyclohexane dimer is a valuable intermediate in the synthetic production of lysine.

II. Description of the Prior Art

The reaction of nitrosyl chloride with olefins has been studied intensively and has played a major role in the structure determination and identification of terpenes. Depending on experimental conditions and olefin structures, the reaction leads to 2-chloro-1-nitrosoalkane dimers, chloro-oximes, chloronitro compounds, dichloro compounds, dichloronitroso compounds and nitro-nitroso compounds.

More specifically, the dimer derived from cyclohexene, 2-chloro-1-nitroso-cyclohexane dimer (CNCD), was first reported by Bayer in 1894. In 1948, R. K. Allison disclosed in U.S. Pat. No. 2,485,180 a significant improvement in the synthesis of CNCD and terpene derived dimers by using liquid $SO_2$ as the reaction solvent at preferred temperatures between −40° and −60°C. By using molar ratios of NOCl to olefin within the ranges of 0.892 to 1.2, relatively low yields (i.e. less than 75%) of dimer, were obtained with the reported poorest yields at molar ratios less than 1.0, and with the remainder of the reaction mixture consisting essentially of undesired addition by-products.

Experimental evidence in the literature indicates that the chloro-nitroso dimer obtained from liquid $SO_2$ solvent is the result of a trans addition of NOCl to the double bond and the structure has accordingly been assigned trans -2,2'-dichlorotrans-azodioxycyclohexane. Further evidence indicates that the Cl—NO interaction is strong in the diaxial form and dipole repulsion equally strong in the equatorial form so as to imply the presence of the following three conformers:

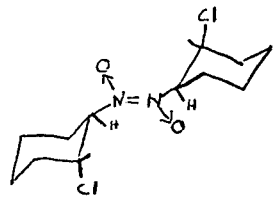

Allison's work has been repeated or modified by Ohno et al. as shown in Tetrahedron, Letters 43, 4047–4052, 1965 and by Yoshida in Tetrahedron, Letters 32, 2763–2766, 1965 wherein dimer yields remain substantially low, i.e. in the range of 60–80 mole percent.

SUMMARY OF THE INVENTION

In accordance with the procedures of the present invention, we have provided a method for the conversion of cyclic olefins to the corresponding nitrosochloride dimers in heretofore unachieved yields of up to 90 mole percent or greater. These yields have been achieved by operating in the absence of oxygen, either in its free form or as peroxidic compounds. In addition to maintaining a substantially oxygen-free environment, we have found that preferred operating conditions also include use of a NOCl/cyclo-olefin ratio of less than 0.95/1 and a gradual addition of the nitrosating agent to the reaction mixture so as to prevent the build up of excess unreacted NOCl in the system.

We have discovered that by maintaining a substantially oxygen-free environment throughout the reaction, the formation of any polysulfone oligomers resulting from the free radical copolymerization of $SO_2$ and the cyclo-olefin is suppressed. For the purposes of this invention, the term "substantially oxygen-free environment" is meant to include the absence of oxygen both as elemental oxygen in the reaction environment and in the form of any peroxidic compounds in the reactant materials. Thus, a substantially oxygen-free environment can be attained by careful purification of the cyclo-olefin and NOCl starting material to remove any peroxides and by exclusion of air during the reaction. We have further found that when formation of the sulfur dioxide-cyclo-olefin polysulfone adduct is suppressed, the ratio of NOCl/cyclo-olefin is lowered to about 0.49–0.92 and the reaction temperature raised without affecting high dimer yields thereby affording substantially greater economy in processing.

Thus, according to this invention, definite and unobvious advantages are derived because by-product formation resulting during the addition of NOCl to cyclo-olefins is substantially reduced and the yield of dimer product correspondingly increased.

DESCRIPTION OF PREFERRED EMBODIMENTS

This invention is directed generally to the nitrosochlorination of a single cyclo-olefin or admixtures thereof particularly to the nitrosochlorination of cycloalkenes and terpene-derived cyclo-olefins, e.g. cyclohexene, cycloheptene, cyclooctene, methyl cyclohexene, 8,9-dihydrolimonene, d-or l-limonene dipentine, α-or β-pinene, or the like. It is advisable that the cyclo-olefin have but one double bond, although cyclo-olefins with a multiplicity of double bonds such as cyclopentadiene may also be used as starting material in accordance with the invention.

Oxygen may be removed from the cyclo-olefin system using any conventional methods, preferably by purging the reaction mixture with nitrogen prior to introduction of NOCl. It is also desirable to treat the cyclo-olefin by washing with a basic reducing medium and distilling under oxygen-free conditions, as for example distilling over metallic sodium under a nitrogen atmosphere. The peroxides may also be readily removed from the NOCl material by passing through an absorbent medium and purging with $N_2$ prior to introduction into the reaction mixture.

Although relatively high yields are obtainable by merely operating in a substantially oxygen and peroxide free environment, we have further found that even higher yields are obtained by carefully controlling the addition of the NOCl reactant to avoid build up of excess unreacted NOCl in the system and by maintaining the rate of conversion of the cyclo-olefin to less than 100%.

The gradual, controlled addition of NOCl is most readily accomplished by utilizing gaseous NOCl or mixtures of gaseous nitrous oxide and chlorine which are fed on a demand basis from a separate vessel into the reaction medium containing the $SO_2$ and cyclo-olefin or by maintaining an atmosphere of NOCl above the surface of the stirred reaction mixture. In general, we have found that the amount of unreacted NOCl in the reaction mixture at any one time should comprise less than about 5% relative to the total amount of NOCl used in the reaction. Addition methods which employ the bubbling of NOCl through the reaction mixture or the use of liquid NOCl are not preferred since these methods result in a high local concentration of unreacted NOCl.

If the presence of unreacted NOCl is to be avoided, it is obvious that the molar equivalent of NOCl present should be less than the molar equivalent of the cyclo-olefin present so that the conversion of the cyclo-olefin is less than 100%, preferably, less than about 92%. In particular, we have found that the use of molar ratios of NOCl to cyclo-olefin in the range of about 0.49:1 to 0.92:1 give superior yields. The presence of excess cyclo-olefin thus ensures that the desired chloronitroso product does not react in a consecutive reaction with NOCl and produce undesired by-products. The unreacted excess cyclo-olefin may be readily recycled together with the solvent.

By utilizing the novel procedure of the present invention, we have been able to obtain the desired yields at reaction temperatures as high as $-10°$ to $-40°C.$, a considerable improvement over previous methods which had preferred operating temperatures of $-40°$ to $-60°C$. The desired temperatures may be obtained by using $SO_2$ as an internal refrigerant and refluxing the liquid solvent under reduced pressure. In such a system, although the heat of reaction between the cyclo-olefin and NOCl is substantial, it is dissipated as the latent heat of vaporization of the $SO_2$. Refrigeration is applied herein only at the surface of the reflux condenser and the condensed $SO_2$ is allowed to return to the reaction mixture.

Recovery of the nitrosochloride dimer after completion of the reaction is most conveniently carried out by diluting with a solvent such as diethyl cellosolve and flash evaporating to remove the $SO_2$ and any excess cyclo-olefin. It is preferred that this flash evaporation be done at low temperatures (i.e. less than about 50°C.) so as to minimize dissociation and isomerization of the dimer to 2-chloro-oxime. The slurry of the chloro-nitroso dimer crystals is cooled and filtered or centrifuged and washed with the same solvent. The combined liquors are sent to a column where solvent and traces of cyclo-olefin are removed and recycled to the reactor. After elimination of by-products, the chloronitroso dimer can be further purified by recrystallization (e.g. from hexane) or it may be further processed, as by reaction with ammonia as required for the desired end-product.

The invention will be further illustrated by the following examples.

EXAMPLE 1 (COMPARATIVE)

This example is presented to show the yield of chloronitroso dimer obtained using the method currently employed in the art.

84g. (1.02 mol) cyclohexene (99 mol % purity) were charged into a one liter, three neck flask equipped with a magnetic stirrer, thermometer, dry ice condenser and nitrogen by-pass. 350ml. liquid $SO_2$ were then condensed directly into the flask and 50ml. NOCl (1.08 mol) distilled in over a period of 20 minutes with the reaction mixture maintained at $-45°C$. The reaction mixture was stirred for an additional 25 minutes at $-50°C.$, then 250ml. methanol were added and the liquid $SO_2$ allowed to distill off at about 25°C. The resulting mixture was crystallized and gave a yield of 73mol % 2-chloro 1-nitroso cyclohexane dimer.

EXAMPLE 2

An air-tight reactor was used consisting of a 500ml. four neck, round bottom flask provided with mechanical stirrer, dry-ice condenser attached to a nitrogen by-pass and bubbler, a thermometer and a gas inlet tube. The reactor was flushed with $N_2$ for one-half hour, then the gas inlet stopcock was closed and the atmosphere of nitrogen maintained by the nitrogen by-pass above the dry-ice condenser. The reactor was then cooled in dry ice, the condenser charged with dry ice-acetone mixture and 250ml. liquid $SO_2$ were condensed into the reactor through the dry-ice condenser, after which 70.63g. cyclohexene (0.8599 mol), which had previously been washed with 10% aqueous NaOH and distilled over metallic Na under a nitrogen atmosphere, were added.

A second round bottom flask of 125ml. capacity, with ball and socket joint surmounting a Teflon stopcock through which a nitrogen by-pass was maintained was cooled. Then 38.47g. NOCl (0.587 mol) was passed through a trap containing $NaNO_2$, then moist KCl and finally $CaCl_2$ and into the second flask.

The NOCl flask was then attached to the delivery system of the first reactor using air-tight connections. The gaseous NOCl was added over a period of 1.28 hr. while the reaction temperature was maintained at $-40°C.$ using a cooling bath. After delivery of the NOCl, the reaction temperature and stirring were maintained for an additional 15 minutes. Then, 100ml. hexane was added and the slurry evaporated at reduced pressure in a flash evaporator. The residue was treated with 500ml. hexane and the solvent again distilled off at reduced pressure to ensure elimination of traces of $SO_2$. The solids were then triturated with 500ml. hexane, the slurry cooled to $-30°C.$ and filtered on a precooled filter. The filter cake was washed with 100ml. of precooled hexane, dried in vacuum and weighed. The filtrate was concentrated and deposited some additional impure CNCD on standing. This was filtered off and the final filtrate was evaporated in a vacuum leaving a greenblue oil. The resulting yield was 80.23g.

representing 89.4 mol% recovery based on the total cyclohexene reacted.

In order to determine the purity of this product, the methanol insoluble materials or polysulfones were isolated by boiling a portion of the crude crystals with methanol for 10 min. and filtering hot. The resulting residue showed only 1.6% methanol insolubles based on the total cyclohexene reacted.

EXAMPLE 3

This example is presented to show that even relatively low NOCl/cyclo-olefin ratios can produce high yields of exceptionally pure chloro-nitroso dimer when the reaction conditions of the present example are maintained.

The procedure of Example 2 was repeated using amounts of NOCl and cyclohexene sufficient to give a molar ratio of 0.49. The reaction temperature was maintained at −40°C. for the 1.65 hours during which the NOCl was added and the reaction occurred. A yield of 85.8% 2-chloro-1-nitroso cyclohexene dimer was obtained. When analyzed for polysulfones, only 3.5% methanol insoluble material was recovered.

EXAMPLE 4 (COMPARATIVE)

This example is presented to show the criticality of operating in an oxygen-free environment in order to suppress formation of undesired polysulfone by-products. The procedure of Example 3 was repeated using an NOCl/cyclo-olefin ratio of 0.49 and temperature of −40°C. but no attempt was made to prevent admission of oxygen and oxygen was admitted to the reaction during the gradual addition of the NOCl. This procedure gave a yield of 93.5% crude product but upon analysis, undesired methanol-insoluble polysulfone by-products were found to represent 14% of this crude product, thus substantially reducing the effective yield of the desired 2-chloro-1-nitroso cyclohexane dimer.

EXAMPLE 5-7

The procedure of Example 2 was repeated varying the molar ratio and temperature conditions employed. The results are shown in Table I together with those obtained in Examples 1–4.

| EXAMPLE | NOCl/C$_6$H$_{10}$ MOL/MOL | TEMP. °C. | TOTAL TIME HOURS | C$_6$H$_{10}$ CONVERSION MOL.% | YIELD BASED ON C$_6$H$_{10}$ | YIELD OF MeOH INSOLUBLES BASED ON C$_6$H$_{10}$ |
|---|---|---|---|---|---|---|
| 1 (comparative) | 1.06 | −45 | 0.75 | 95 | 73 | — |
| 2 | 0.68 | −40 | 1.63 | 69.4 | 89.4 | 1.6 |
| 3 | 0.49 | −40 | 1.65 | 51.8 | 85.8 | 3.5 |
| 4 (comparative) | 0.49 | −40 | 1.65 | 49.3 | 93.5 | 14.0 |
| 5 | 0.81 | −40 | 2.25 | 81 | 88.3 | 0 |
| 6 | 0.59 | −40 | 1.75 | 63.2 | 84.6 | 7.2 |
| 7 | 0.67 | −30 | 1.75 | 67 | 89.6 | 0 |

EXAMPLE 8

The procedure of Example 2 can be carried out using the cyclo-olefins listed in Table II instead of cyclohexene thereby producing the corresponding chloronitroso products.

Table II

Cyclo-olefin
Cyclo-octene
Cycloheptene
d-limonene
1-methyl cyclohexene
cyclopentadiene

I claim:

1. In a process for the nitrosochlorination of cyclo-olefins wherein a cyclo-olefin is dissolved in liquid sulfur dioxide and contacted with NOCl at a reaction temperature below −10°C, the improvement which comprises maintaining a substantially oxygen-free environment throughout the reaction by excluding air and peroxides and thereafter separating the resulting nitrosochloride.

2. The process of claim 1 wherein the reaction mixture is purged with nitrogen prior to introduction of the NOCl.

3. The process of claim 1 wherein the molar ratio of NOCl to cyclo-olefin is in the range of about 0.49:1 to 0.92:1.

4. The process of claim 1 wherein the NOCl is added gradually to the mixture to prevent build up of free NOCl in the mixture.

5. The process of claim 1 wherein the temperature is maintained at about −10° to −40°C.

6. The process of claim 1 wherein the cyclo-olefin is cyclohexene.

* * * * *